United States Patent [19]
Burk et al.

[11] Patent Number: 5,196,715
[45] Date of Patent: Mar. 23, 1993

[54] OPTICAL SURFACE INSPECTION OF WEB WITH STREAK SIGNAL GENERATING MEANS

[75] Inventors: Gary N. Burk, Powell; Mark A. Miller, Columbus, both of Ohio

[73] Assignee: ABB Process Automation Inc., Columbus, Ohio

[21] Appl. No.: 786,318

[22] Filed: Oct. 31, 1991

[51] Int. Cl.$^5$ .................................. G01N 21/88
[52] U.S. Cl. ................................... 250/562; 250/572
[58] Field of Search .............. 250/562, 563, 571, 572; 356/430, 431

[56] References Cited

U.S. PATENT DOCUMENTS 3,618,063  2/1970  Johnson ........................ 250/563
4,075,498  2/1978  Takasuka et al. .............. 250/562
5,118,195  6/1992  Dobbie ......................... 250/572

Primary Examiner—David C. Nelms
Attorney, Agent, or Firm—Paul J. Lerner

[57] ABSTRACT

An apparatus for detecting streaks in a moving sheet of material utilizes the signal generating and processing means of an existing spot/hole detection system which provides a series of spot measurement signals generated sequentially as a machine direction series of cross-machine sets and assigns a cross-direction location to each signal. Means are provided for calculating an exponential average of the signals for each of the cross-machine locations. This average is compared with a predetermined standard and an output signal, including a cross-machine location, is generated when the average exceeds the standard.

9 Claims, 5 Drawing Sheets

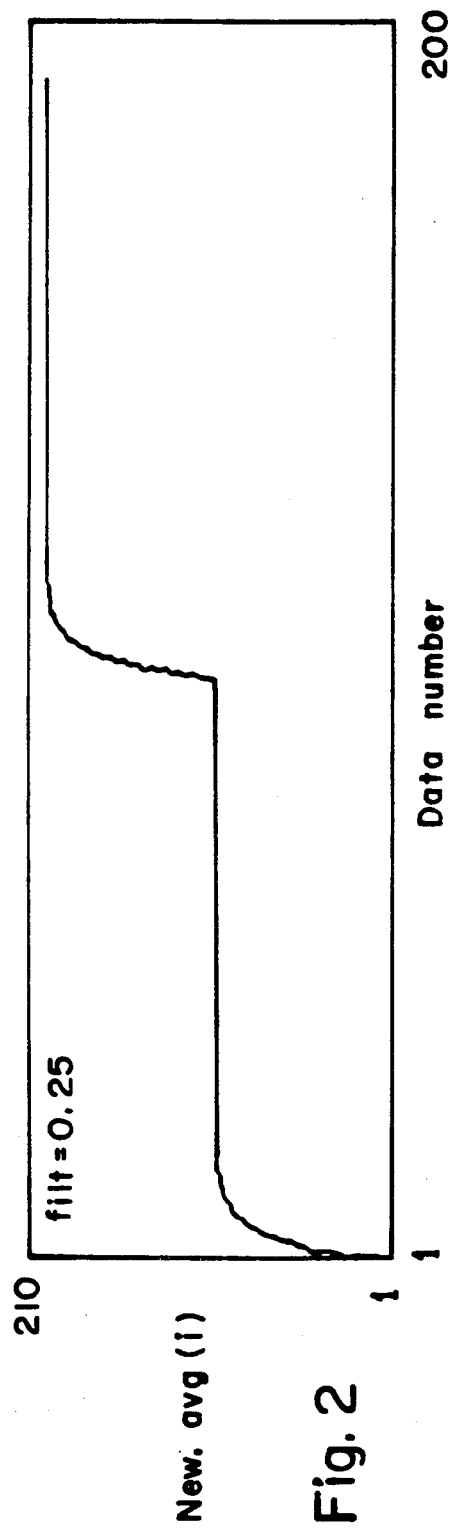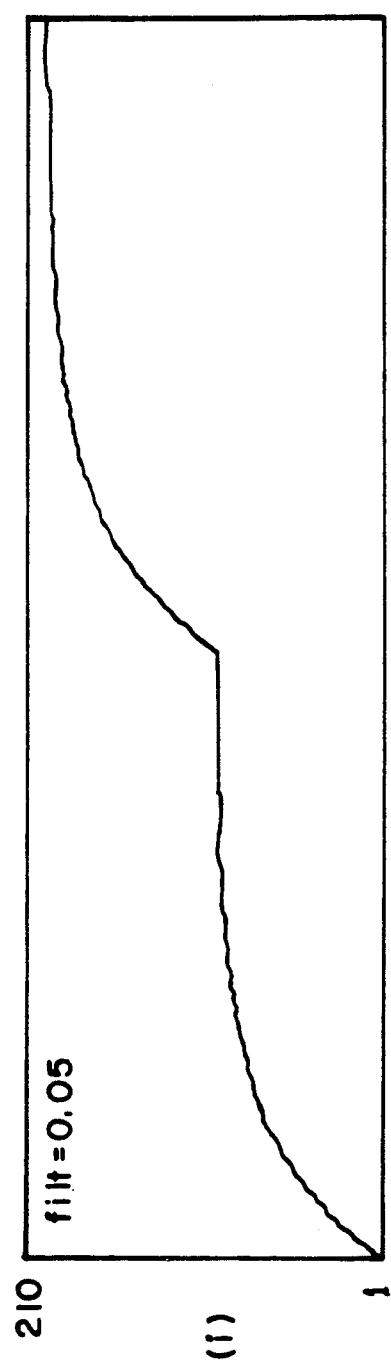
Fig. 2
Fig. 3

OPTICAL SURFACE INSPECTION OF WEB WITH STREAK SIGNAL GENERATING MEANS

BACKGROUND OF THE INVENTION

The present invention pertains to the inspection of moving sheet material and, more particularly, to apparatus for detecting a streak extending in the machine direction of the sheet.

Optical scanners have been used to inspect sheet material moving as a continuous web in a high-speed production line at rates in excess of 100 meters per minute. The material can be, for example, paper, plastic, or metal. Such scanners may be set up to inspect the material for any number of characteristics which are measured by illuminating the material and comparing the intensity of light reflected or transmitted therefrom with threshold levels. A common type of optical scanner includes an array of photosites, each providing a pixel signal having a magnitude representing the intensity of light received from a corresponding point on the sheet material. Each photosite corresponds to the location of the point on the sheet material being inspected. The length of the array corresponds to the width of the sheet material, inspected by that array, so that the photosites provide successive sets of pixel signals, each set corresponding to a scan of the width of the sheet material, with succeeding sets progressing along the sheet in the machine direction. Such systems, which are particularly adapted to detect spots or holes in the sheet, are known as spot/hole systems.

Oftentimes, it is desired to detect persistent marks or streaks, on the sheet, extending in the machine direction. If of adequate optical contrast, such streaks will be detected by conventional inspection systems and represented as a series of spots in a machine-direction line. However, if the streak contrast is lower than the normal optical variation, or "noise", of the material being inspected, it will not be detected by presently available spot/hole detection equipment.

Using a clay coated paper manufacturing process as an example, streaks are easily produced in the clay coating. However, these streaks often alter the transmissivity of the sheet by an amount smaller than the normal point-to-point transmissivity variation of the paper, known as "optical formation". Detection of such streaks is presently accomplished by utilizing a separate set of detectors and sampling them at a low rate so as to allow a significant length of paper to be included in each sample. Formation induced transmissivity variations tend towards zero as the sample length increases, whereas the signal variation produced by the streak will persist; i.e., the formation noise average approaches zero, while the streak induced component of the signal does not. As a result, the signal representing the streak has greater contrast, allowing its detection. This method of streak detection requires: a separate timing means, a separate set of detectors, a separate means for controlling the light intensity used by those detectors, and a separate means for processing the signals. In addition to the cost of these separate items, the separate detectors occupy critical space in the process area.

It is, therefore, an object of the invention to provide an improved apparatus for optically detecting streaks in a moving sheet of material, the apparatus being effective to detect streaks when the streak contrast is lower than the normal optical variation of the material being inspected.

It is a further object of the invention to provide an improved streak detection apparatus, of the character above-described, which utilizes detectors and associated hardware already emplaced as components of a spot/hole detection system.

It is yet another object to provide a streak detection apparatus which requires a minimum of computer storage capacity and which operates in conjunction with, and at the same speed as a conventional spot/hole detection system.

SUMMARY OF THE INVENTION

Briefly stated, the foregoing and other objects and advantages of the invention as may hereinafter appear are achieved by an inspection apparatus which utilizes the signal generating and processing means of an existing spot/hole detection system which provides a series of pixel signals each having a magnitude representing the intensity of electromagnetic radiation received from a corresponding point on a sheet of material. These signals are generated sequentially as a machine-direction series of cross-machine sets, each signal being assigned a cross-direction location. Means are provided for calculating an exponential average of the signals for each of the cross-machine locations. This average is then compared, in a comparison means, with a predetermined standard and an output signal, including a cross-machine location, is generated by an output generating means when the average exceeds or is less than the standard.

In keeping with an aspect of the invention, the exponential average is calculated in accord with one of the following formulae:

Eq. a)

$$NewAvg = (NewPixel - OldAvg)/N + OldAvg$$

or

Eq. b)

$$NewAvg = (N \cdot OldAvg + NewPixel)/(N+1)$$

where:
NewAvg is the new exponential average pixel value
OldAvg is the old exponential average pixel value
NewPixel is the signal value of the last pixel being included in the average
N is a filter constant

BRIEF DESCRIPTION OF THE DRAWING

FIG. 2 is a plot of an exemplary exponential average.

FIG. 3 is a plot of a second exemplary exponential average.

DESCRIPTION OF THE PREFERRED EMBODIMENT

Figure 1:
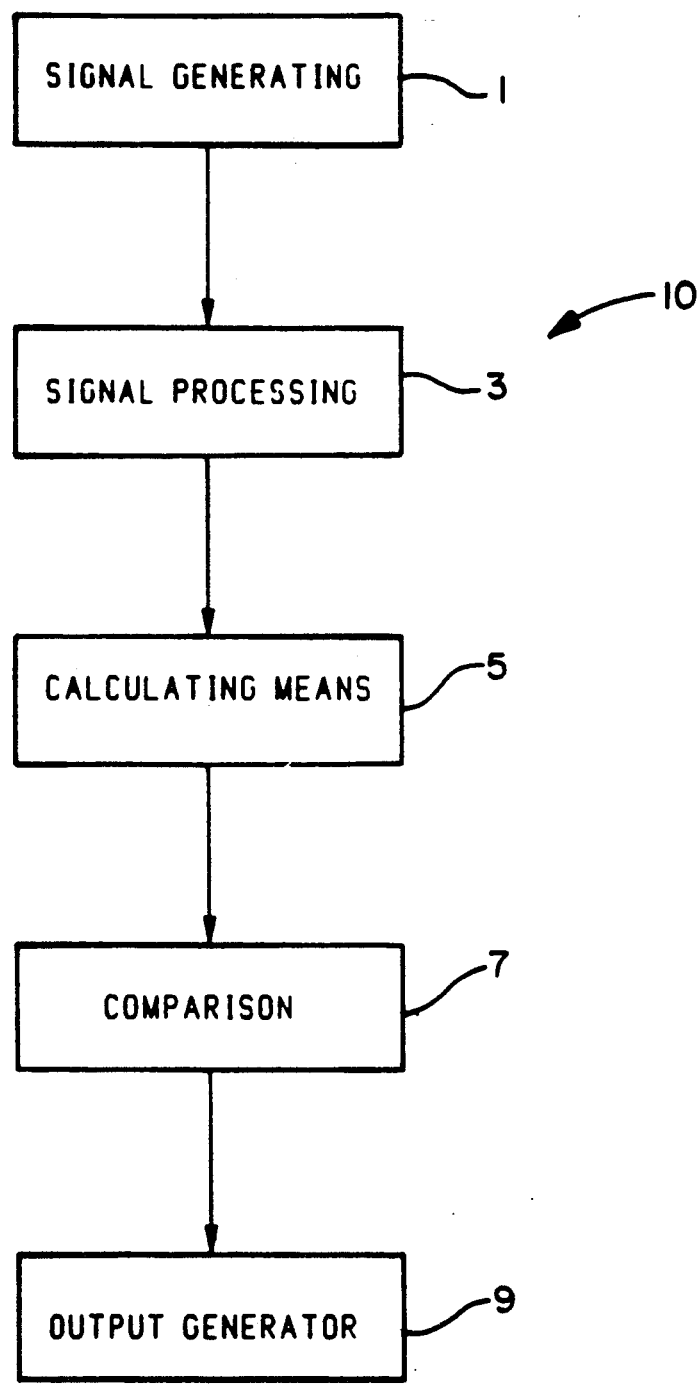
FIG. 1 is a block diagram of a streak detection apparatus in keeping with the present invention.

Referring to FIG. 1, apparatus for inspecting moving sheet material is indicated generally at 10 and comprises signal generating means 1 for providing a plurality of pixel signals, each having a magnitude representing the intensity of electromagnetic radiation received from a corresponding point on the moving sheet. The pixel signals are generated sequentially, as a series of cross-machine sets, with consecutive series extending in the machine direction. The signals are received by a signal processing means 3 which assigns a cross-direction address or location to each signal of a set. Signal generating and processing means, such as the above-described, are presently used in spot/hole detection systems of the type disclosed in U.S. Pat. No. 4,950,911 which includes a detailed description of one such system.

Signals form signal processing means 3 are received by a calculating means 5 which calculates an exponential average of the signals for each of the cross-machine locations. This exponential average is compared, in a comparison means 7, with predetermined standards and an output signal, including a cross-machine location, is generated by an output generating means 9 when the average exceeds the standards.

A basic equation for an exponential average is:

$$New.avg = (1 - filt)*Old.avg + filt*Data\ (i)$$

$$Old.avg = New.avg$$

where: filt is the amount of the new data to be added to the existing average so as to create the new average. Thus, for example, if filt=0.25, then (1−filt)=0.75. In this example, if Old.avg was 100, and the next data point Data (i)=116, then $$New.avg = 0.75*100 + 0.25*116 = 75 + 29 = 104$$

so that the new average is 104, which becomes the old average when the next data point becomes available. If the next data Data (i+1) is also 116, then $$New.avg = 0.75*104 + 0.25*116 = 107$$

If the succeeding new data points continue to equal 116, then the exponential average will be successively: 100, 104, 107, 109.25, 110.94, 112.20, 113.15, 113.86, 114.39, 114.79, 115.09, 115.31, 115.48, 115.61, 115.71, 115.78, 115.83 . . . .

FIG. 2 illustrates how the new average varies with each data point, where the average starts at 0, and the data consists of 100 data points of 100, followed by 100 data points of 200, and the filter factor is 0.25. It is seen that each new average moves 25% of the separation or spread between the old average and the new data point. The same data stream is used to calculate the average illustrated in FIG. 3, but with the filter factor reduced to 0.05.

Figure 4:
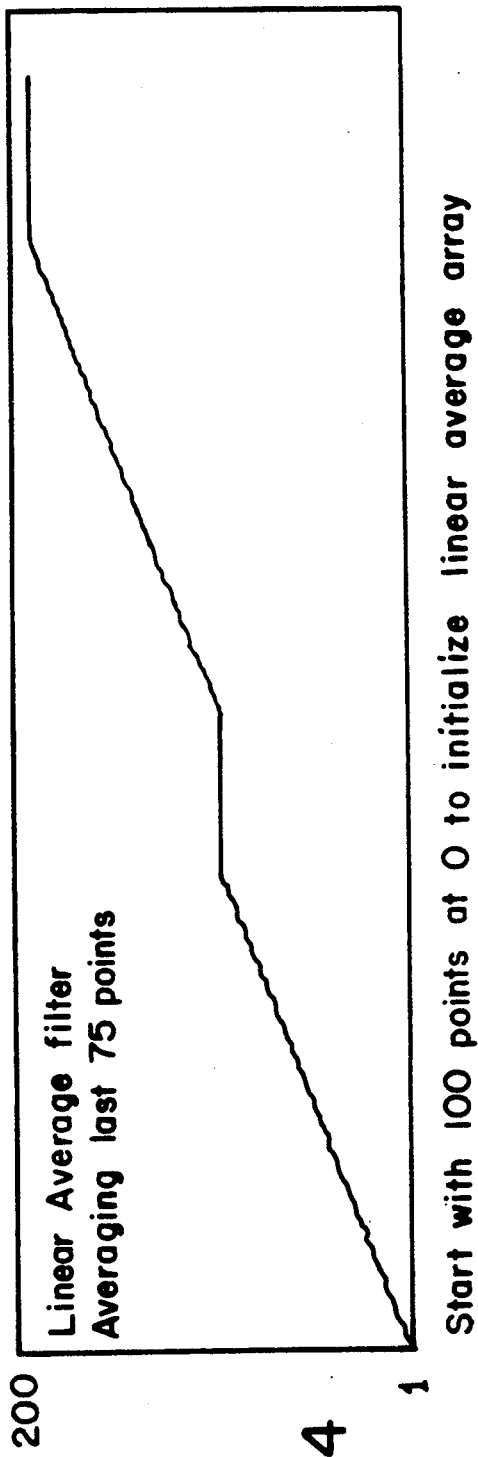
FIG. 4 is a plot of an exemplary arithmetic average.

In FIG. 4, there is illustrated a running arithmetic average of the last 75 data points used to calculate New.avg. Since 75 data points are required for the calculation of the arithmetic average, 74 data values of "0" were added to the data stream. It will be observed that the running arithmetic average of 75 terms settles at the new value in approximately the same time interval (as measured by the number of data points) as does the corresponding exponential average with a filter factor of 0.05. However, calculation of the exponential average requires 3 number storage locations, whereas calculation of the arithmetic average requires 78 locations such locations (75 of which contain old data points). This difference of 75 storage locations per value averaged, multiplied by the 32,767 pixels in a single cross-machine set of an AccuRay sheet inspector, comprises a difference of about 2.5 megawords of memory. Further, arithmetic averaging requires, with each new calculation, the subtraction of the oldest data point and the addition of the newest data point to the old data storage, in addition to the calculation of the new average, whereas exponential averaging discards old data and, therefore, has no housekeeping to perform. Finally, exponential averaging may be performed entirely in hardware, and, thus, may be done at the required rate of 10 million new averages per second. Although exponential averaging does not yield an identical result to arithmetic averaging, it may be "tuned", through the selection of an appropriate filter factor, to approach that value to whatever degree of precision is required. It is also equally effective in removing the effects of random point-to-point noise, so that small variations in the mean value of a series of data points may be detected. By way of example, in a sheet of nominal fine bond paper, the point-to-point noise produced by paper formation effects might be ±5% of the data signal, whereas a streak in the clay coating might cause a persistent machine-direction variation of only 1% in the average signal level. Because random noise is reduced, in a data average, by the square root of the number of samples included in the average, averaging 100 points will reduce the noise effect from ±5% to ±0.5%, while the streak variation, being consistent, will not be reduced and will, therefore, remain 1%. By this means, a streak that is buried in the background noise for a single sample (signal to noise ratio of 1:5), will be detectable in an average of 100 samples as its signal to noise ratio will be 2:1.

Applying the equation for an exponential average to the output of signal processing means 3

$$NewAvg = [N*OldAvg + NewPixel]/(N+1) \qquad (1)$$

$$OldAvg = NewAvg$$

where:
NewAvg is the new exponential average pixel value
OldAvg is the old exponential average pixel value
NewPixel is the signal value of the last pixel being included in the average
N is the filter factor
If we let $$M = N + 1 \qquad (2)$$

Then $$NewAvg = [(M-1)*OldAvg + NewPixel]/M \qquad (3)$$

Rearranging algebraically yields $$NewAvg = (NewPixel - OldAvg)/M + OldAvg \qquad (4)$$

or $$NewAvg = [(NewPixel - OldAvg) + M*OldAvg]/M \qquad (5)$$

It is to be noted that the "/(N+1)" term has been eliminated, thus allowing integer binary filter factors to be performed by bit-shifting and so providing effectively "instantaneous" calculation.

Figure 5:
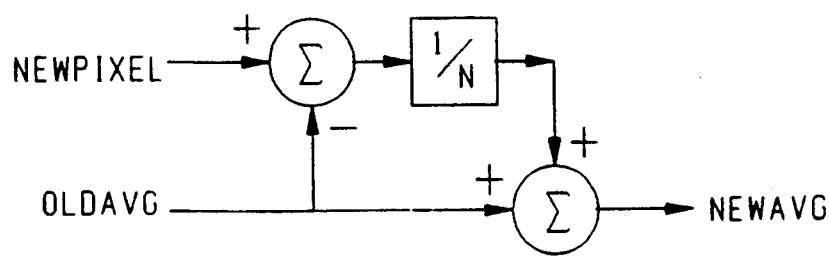
FIG. 5 is a schematic view of a circuit for calculating an exponential average.
Figure 5:
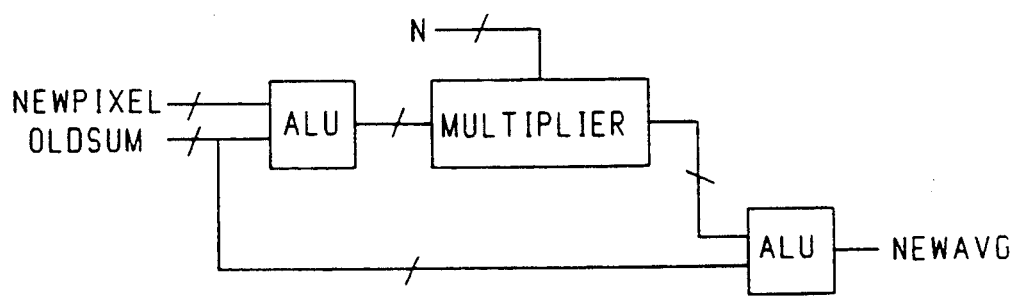
Figure 6:
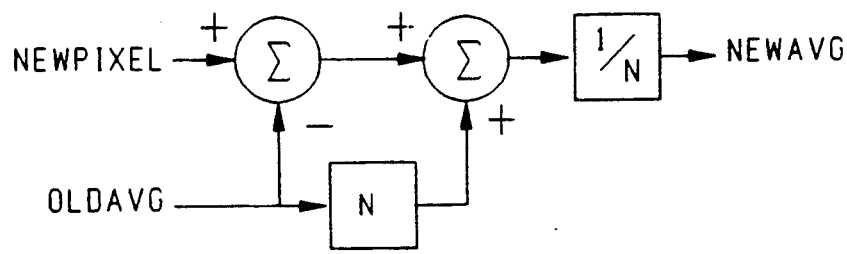
FIG. 6 is a schematic view of a second circuit for calculating an exponential average.
Figure 6:
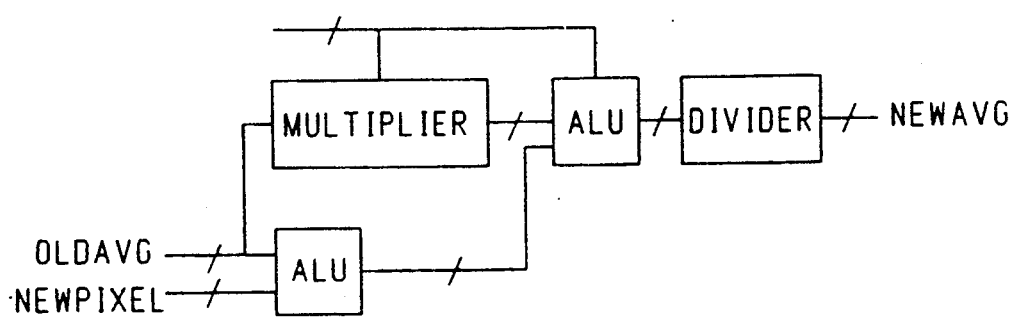

Although equations (4) and (5) yield the same mathematical result, they offer differing advantages and disadvantages with respect to electronic implementation. Both equations, however, may be easily implemented with current ALU (Arithmatic Logic Unit) modules. To avoid the requirement of floating point arithmetic and to reduce the math operations required, integer multipliers are used, rather than decimal. Further, if $N=1, 2, 4, 8, 16 \ldots 2^k$, where k is an integer, in equation 5, may be accomplished by bit shifting and so may be hardwired, requiring no components and no real-time to execute. There are shown, in FIGS. 5 and 6 respectively, circuits implementing equations (4) and (5).

Figure 7:
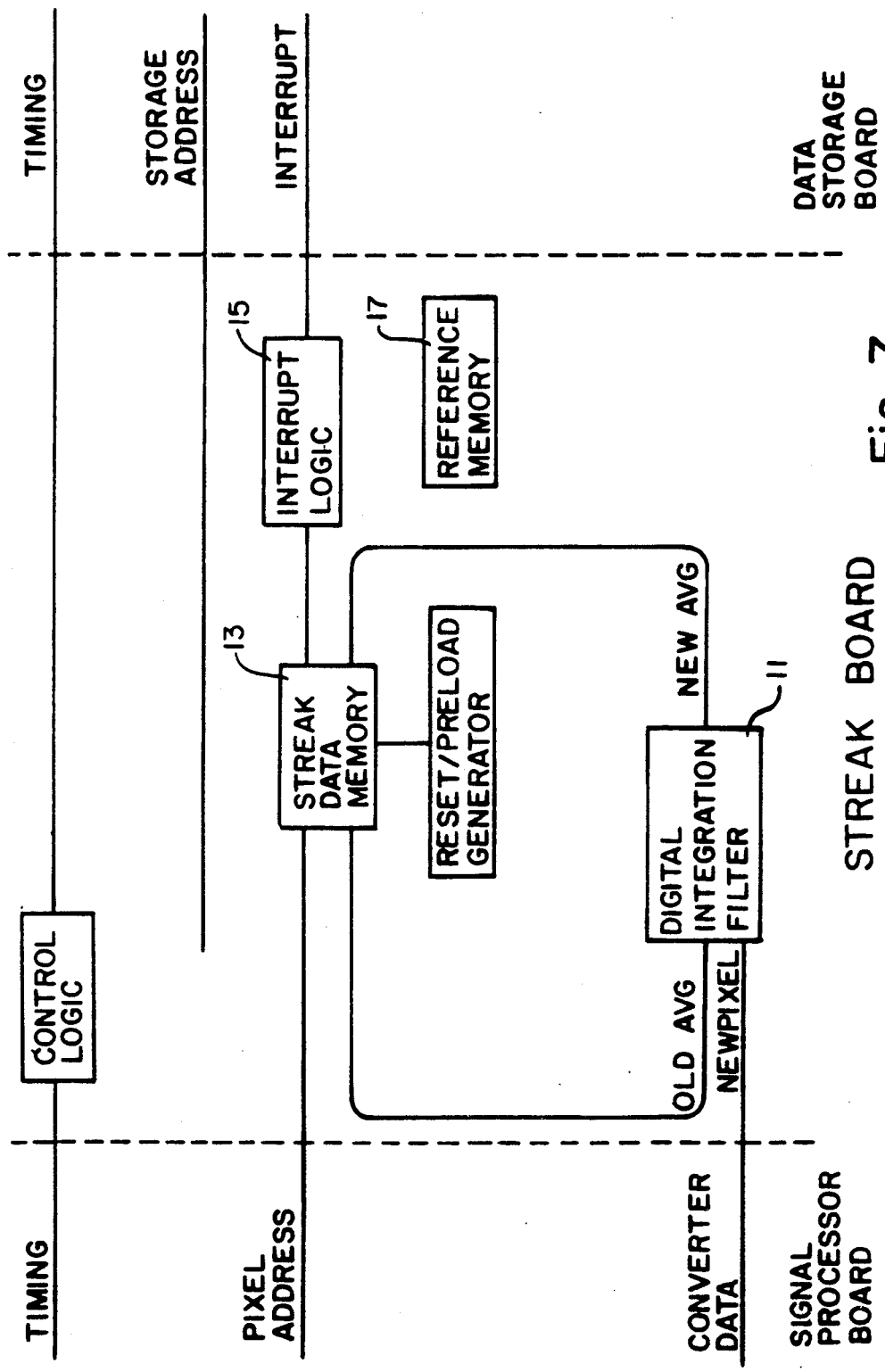
FIG. 7 is a block diagram of a circuit board including calculating, comparing and output elements.

In FIG. 7, there is shown a block diagram of a circuit board for the present apparatus, specifically adapted for use in conjunction with the signal processor board and the data storage board of the spot/hole detection device disclosed in U.S. Pat. No. 4,950,911. In this configuration, data from signal processor 3 is exponentially averaged by a Digital Integration Filter 11 and the average, for each cross-machine pixel position, is saved in a Streak Data Memory 13. These averages are tested by the Interrupt Logic 15 which receives a set of upper and lower thresholds from the Reference Memory 17 and outputs an event signal and a pixel position address if the average is out of limits.

Having described the invention with reference to a preferred embodiment, it will be apparent to one of ordinary skill in the art that various modifications and alterations may be made thereto without departing from the spirit and intent of the invention which are intended to be limited in scope only by the appended claims.

We claim:

1. In a material inspection apparatus for use in a sheet forming machine, said apparatus being of the type including:

detecting means for providing a plurality of pixel signals, each having a magnitude representing the intensity of electromagnetic radiation received from a corresponding point on a moving sheet of material, said signals being generated sequentially as a series of cross-machine sets, said series extending in the machine direction; and calculating means for calculating an exponential average of the signals for each of said cross-machine locations;

comparison means for comparing said exponential average for each of said cross-machine locations to a predetermined standard; and output generating means for generating a streak signal when said exponential average exceeds said predetermined standard, said streak signal including a cross-machine location.

2. The apparatus of claim 1, wherein said calculating means calculates said exponential average in accord with the following formula:

$$NewAvg = (NewPixel - OldAvg)/N + OldAvg$$

where:
   NewAvg is the new exponential average pixel value
   OldAvg is the old exponential average pixel value
   NewPixel is the signal value of the last pixel being included in the average
   N is a filter constant 3. The apparatus of claim 1, wherein said calculating means calculates said exponential average in accord with the following formula:

$$NewAvg = [(NewPixel - OldAvg) + N*OldAvg]/N$$

where:
   NewAvg is the new exponential average pixel value
   OldAvg is the old exponential average pixel value
   NewPixel is the signal value of the last pixel being included in the average
   N = a filter constant 4. The apparatus of claim 1, wherein said calculating means includes a /N microchip.

5. The apparatus of claim 1, wherein said calculating means includes a (N−1) * microchip.

6. The apparatus of claim 2, wherein N is an integer.

7. The apparatus of claim 3, wherein N is an integer.

8. The apparatus of claim 2, wherein $N=2^x$ and x is an integer.

9. The apparatus of claim 3, wherein $N=2^x$ and x is an integer.

* * * * *